(12) United States Patent
Meyer Zu Berstenhorst et al.

(10) Patent No.: US 8,715,406 B2
(45) Date of Patent: May 6, 2014

(54) UV ABSORBERS SOLUBLE IN POLAR MEDIA

(75) Inventors: Birgit Meyer Zu Berstenhorst, Moers (DE); Serguei Kostromine, Swisttal-Buschhoven (DE)

(73) Assignee: Bayer MaterialScience AG, Leverkusen (DE)

( * ) Notice: Subject to any disclaimer, the term of this patent is extended or adjusted under 35 U.S.C. 154(b) by 49 days.

(21) Appl. No.: 13/318,182

(22) PCT Filed: Apr. 29, 2010

(86) PCT No.: PCT/EP2010/002631
§ 371 (c)(1),
(2), (4) Date: Dec. 5, 2011

(87) PCT Pub. No.: WO2010/127805
PCT Pub. Date: Nov. 11, 2010

(65) Prior Publication Data
US 2012/0094127 A1    Apr. 19, 2012

(30) Foreign Application Priority Data

May 4, 2009  (DE) .................. 10 2009 019 493

(51) Int. Cl.
| C04B 35/624 | (2006.01) |
| C04B 24/42 | (2006.01) |
| C09D 201/00 | (2006.01) |
| B32B 17/06 | (2006.01) |
| B32B 18/00 | (2006.01) |
| B32B 27/36 | (2006.01) |
| C08K 5/544 | (2006.01) |
| C04B 103/60 | (2006.01) |

(52) U.S. Cl.
CPC ............ C09D 201/00 (2013.01); C08K 5/5442 (2013.01); C04B 35/624 (2013.01); C04B 24/42 (2013.01); C04B 2103/605 (2013.01); B32B 17/06 (2013.01); B32B 18/00 (2013.01); B32B 27/365 (2013.01); B32B 2605/006 (2013.01); B32B 2369/00 (2013.01); B32B 2307/748 (2013.01); B32B 2307/412 (2013.01)
USPC ....................................... 106/287.11; 501/12

(58) Field of Classification Search
USPC ........... 106/287.15, 287.11; 501/12; 428/412, 428/429, 447
See application file for complete search history.

(56) References Cited

U.S. PATENT DOCUMENTS

| 4,101,513 A | 7/1978 | Fox et al. | |
| 5,041,313 A | 8/1991 | Patel | |
| 5,391,795 A | 2/1995 | Pickett | |
| 5,679,820 A | 10/1997 | Pickett et al. | |
| 6,060,543 A * | 5/2000 | Bolle et al. ..................... | 524/100 |
| 6,225,384 B1 | 5/2001 | Renz et al. | |
| 7,169,949 B2 | 1/2007 | Boisseau et al. | |
| 2006/0074153 A1* | 4/2006 | Boisseau et al. .............. | 524/100 |
| 2006/0234061 A1 | 10/2006 | Buckel et al. | |
| 2007/0104956 A1 | 5/2007 | Grandhee | |

FOREIGN PATENT DOCUMENTS

| CA | 2 062 217 A1 | 9/1992 |
| DE | 2804283 A1 | 8/1978 |
| EP | 0339257 A2 | 11/1989 |
| EP | 0 570 165 A2 | 11/1993 |
| EP | 0 863 145 A2 | 9/1998 |
| EP | 0931820 A1 | 7/1999 |
| WO | WO-00/66675 A1 | 11/2000 |
| WO | WO-2006/039021 A1 | 4/2006 |
| WO | WO-2006/108520 A1 | 10/2006 |
| WO | WO-2008/071363 A2 | 6/2008 |
| WO | WO-2008/109072 A1 | 9/2008 |

* cited by examiner

*Primary Examiner* — David M Brunsman
(74) *Attorney, Agent, or Firm* — Novak Druce Connolly Bove + Quigg LLP

(57) ABSTRACT

The invention relates to triazine-based special organic UV absorbers modified in such a way as to be soluble in polar coating compositions. The invention further relates to coatings, e.g. sol-gel based ones, containing said novel UV absorbers as well as to the use of said coatings for permanently protecting materials, especially plastics, from photochemical degradation.

19 Claims, No Drawings

UV ABSORBERS SOLUBLE IN POLAR MEDIA

CROSS-REFERENCE TO RELATED APPLICATIONS

This application is a national stage application (under 35 U.S.C. §371) of PCT/EP2010/002631, filed Apr. 29, 2010, which claims benefit of German application 10 2009 019 493.2, filed May 4, 2009, both of which are incorporated herein by reference in their entirety for all their useful purposes.

BACKGROUND

The present invention relates to organic UV absorbers which are soluble in polar media, to lacquer systems prepared therefrom, and to coatings containing such UV absorbers, and to finished parts protected by protective lacquers containing such UV absorbers.

For exterior use, plastics or natural materials (wood) must be protected against photochemical degradation with a suitable coating. To that end, UV-protective agents are added to the plastics themselves, or the materials are provided with covering/protective layers containing UV-protective agents. A very good class of UV absorbers according to the current prior art are biphenyl-substituted triazines (WO 2006/108520 A). This class of substances exhibits an excellent absorbing action at 320-380 nm and at the same time very high intrinsic UV stability (WO 2000/066675 A1, U.S. Pat. No. 6,225,384). Because of their very pronounced aromatic nature, the substances of this class known hitherto are readily soluble only in non-polar and medium-polar media, which is sufficient for most UV-curing protective lacquers based purely on organic substances. It is known that such lacquer layers do not have sufficient scratch resistance. This limits considerably the applications of the systems in the exterior sector, such as, for example, in the architectural sector, and prevents completely some exterior applications, for example as automotive glazing in the driver's field of vision.

If, however, the material is also to be effectively protected against wear and scratches by the protective layer, sol-gel silicate lacquers (see e.g. EP-A 0 339 257, U.S. Pat. No. 5,041,313) and other hybrid lacquers (EP-A 0 570 165) are current prior art. The property profile of the organosilane-based lacquers additionally includes excellent weather and light stability, resistance to heat, alkali, solvents and moisture. However, non-polar additives are not soluble in such lacquer systems; commercially available moderately polar, mostly hydroxy-containing UV absorbers and/or inorganic UV absorbers, such as titanium dioxide, zinc oxide or cerium dioxide, are used as UV absorbers, but these do not have the optimum action (EP-A 0 931 820). UV absorbers modified with an alkoxysilyl(alkyl) group for such resorcinol-based lacquer systems have been disclosed in U.S. Pat. No. 5,391,795 and U.S. Pat. No. 5,679,820. However, the mono-modification described therein cannot be transferred to biphenyl-substituted triazines either in terms of the synthesis route or in terms of effect. U.S. Pat. No. 7,169,949 discloses triazine-based UV absorbers which are modified with a silane group. However, the monoalkoxysilyl-substituted triazines described and shown therein do not carry biphenyl substituents. The use of those triazines in organic coating compositions is described. Organic-inorganic hybrid lacquers, in particular sol-gel coatings, are not mentioned, however. As is shown hereinbelow, these monoalkoxysilyl-substituted triazines are not soluble in such lacquers. Moreover, the polar-modified triazines shown here cannot be prepared by the synthesis route proposed in U.S. Pat. No. 7,169,949. Furthermore, the UV-protective action of the non-biphenyl-substituted triazines described therein is not optimal for polycarbonate in particular.

Suitably polar-modified UV absorbers from the substance class of the triazines and their use in lacquer systems, such as hybrid lacquers, in particular sol-gel silicate lacquers, are accordingly not known hitherto.

DESCRIPTION OF PREFERRED EMBODIMENTS

An object of the present invention was, therefore, to provide UV absorbers of triazines which are so substituted and modified that they are both soluble in hybrid lacquers, in particular sol-gel lacquers, and have very a good UV-absorbing quality. It was a further object of the present invention to provide coating systems based on polar substances which, after application to a suitable substrate, such as, for example, a plastics material, can be cured and exhibit an effective and lasting UV-protective action with high weathering resistance.

Coating compositions within the scope of the present invention are defined as compositions containing lacquers or coating substances which in combination form a common lacquer structure. Coating substances are any products of the lacquers and paints industry (see in this connection also: "Lack von A bis Z" Paolo Nanetto, Vinzentz, Hanover 2007). Although the term "lacquer" elsewhere frequently refers only to the outer, visible layer of the lacquer structure, the terms lacquer and coating substances are generally, and also in the case of the present invention, used synonymously.

In the present invention, the term "coating" is synonymous with one or more cured lacquer layer(s) or also coloured and/or printed layer(s) and/or further functional layers.

Polar lacquers within the scope of the present invention are lacquers the coating substances of which are dissolved predominantly in polar solvents (mainly alcohols such as, for example, methanol, ethanol, isopropanol, butanol).

Sol-gel lacquers within the scope of the present invention are lacquers which are prepared by the sol-gel process. The sol-gel process is a process for the synthesis of non-metallic inorganic or hybrid-polymeric materials from colloidal dispersions, the so-called sols.

Hybrid lacquers within the scope of the present invention are based on the use of hybrid polymers as binders. Hybrid polymers (hybrids: lat. "of two different origins") are polymeric materials in which structural units of different material classes are combined at molecular level. As a result of their structure, hybrid polymers can exhibit completely novel property combinations. Unlike composite materials (defined phase boundaries, weak interactions between the phases) and nanocomposites (use of nano-scale fillers), the structural units of hybrid polymers are linked together at molecular level. This is achieved by chemical processes such as, for example, the sol-gel process, with which inorganic networks can be built up. By the use of organically reactive precursors, for example organically modified metal alkoxides, organic oligomer/polymer structures can additionally be produced. Acrylate lacquers containing surface-modified nanoparticles, which form an organic/inorganic network after curing, are likewise defined as a hybrid lacquer.

It was possible, surprisingly, to achieve the object of the present invention by means of triazine compounds of the general formula (I):

$$A-X(-T-Q-P)_n \tag{I}$$

wherein
A is

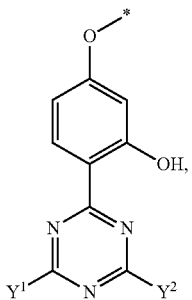

wherein
$Y^1$ and $Y^2$ independently of one another are substituents having the general formulae

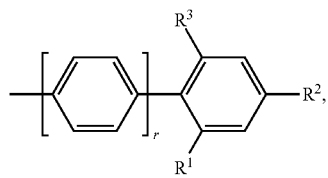

wherein
r is 0 or 1 and is preferably 1,
$R^1$, $R^2$, $R^3$ independently of one another are H, OH, C1-20 alkyl, C4-12 cycloalkyl, C2-20 alkenyl, C1-20 alkoxy, C4-12 cycloalkoxy, C2-20 alkenyloxy, C7-20 aralkyl, halogen, —C≡N, C1-5 haloalkyl, —SO2R', —SO3H, —SO3M (M=alkali metal), —COOR', —CONR'R", —OCOOR', —OCOR', —OCONHR', (meth)acrylamino, (meth)acryloxy, C6-12 aryl (optionally substituted by C1-12 alkyl, C1-12 alkoxy, CN and/or by halogen), C3-12 heteroaryl (optionally substituted by C1-12 alkyl, C1-12 alkoxy, CN and/or by halogen) and wherein
R' and R" denote —H, C1-20 alkyl, C4-12 cycloalkyl, C6-12 aryl (optionally substituted by C1-12 alkyl, C1-12 alkoxy, CN and/or by halogen) or C3-12 heteroaryl (optionally substituted by C1-12 alkyl, C1-12 alkoxy, CN and/or by halogen),
X is a linear or branched linker, characterised in that between the O atom of group A and each T group there is a chain of at least 4 atoms selected from carbon, oxygen, nitrogen, sulfur, phosphorus and/or silicon in the chain. For example, it can be an (optionally substituted) hydrocarbon chain —(CR$_2$)—$_j$, wherein j is an integer greater than 3, or it can be a hydrocarbon chain interrupted by O, N, S, P and/or Si and optionally substituted by one or more, also different, substituents, for example a —CR$_2$—(C=O)—O—CR$_2$— chain. The substituents R, independently of one another, preferably represent H or alkyl radicals.
T is a urethane group —O—(C=O)—NH— or a urea group —NH—(C=O)—NH—, preferably a urethane group —O—(C=O)—NH—,
Q is —(CH$_2$)$_m$—, wherein m is 1, 2 or 3,
P represents a mono-, di- or tri-alkoxysilane group, wherein alkoxy preferably represents methoxy, ethoxy or (2-methoxy)-ethoxy, and
n denotes an integer from 1 to 5.

Of the compounds of the general formula (I), preference is given to the compounds of the general formula (II):

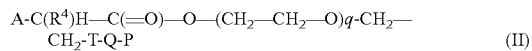

accordingly (II)

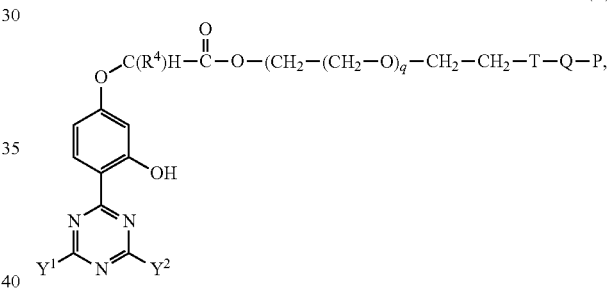

wherein $R^4$ denotes —H or C1-20 alkyl and q is 0, 1, 2 or 3.
Preference is likewise given to the compounds of the general formula (I) wherein n≥2 (formula III)

A-X(-T-Q-P)$_{n≥2}$ (III).

In formulae (II) and (III), A, $Y^1$, $Y^2$, X, T, Q and P have the meanings described under formula (I).

A synthesis route to such triazines which also permits the preparation of the hitherto unknown polar-modified biphenyl-substituted triazines has been developed.

Of the compounds of the general formula (I), the following compounds are particularly preferred:

(I.1)

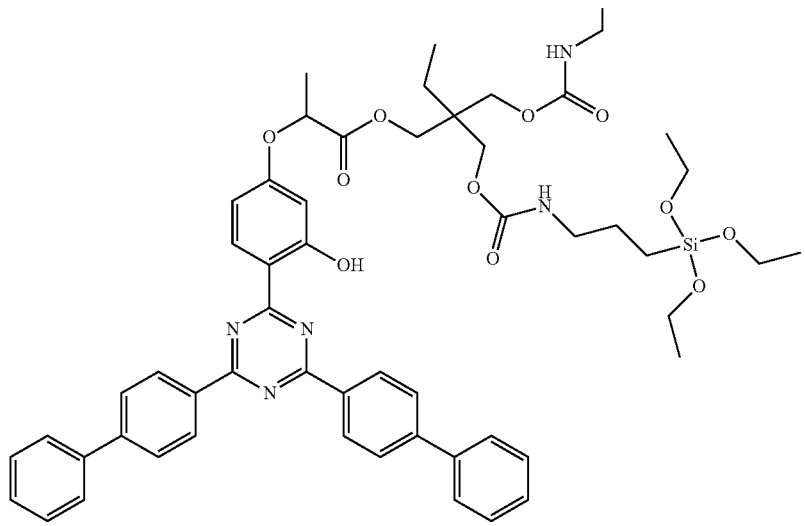
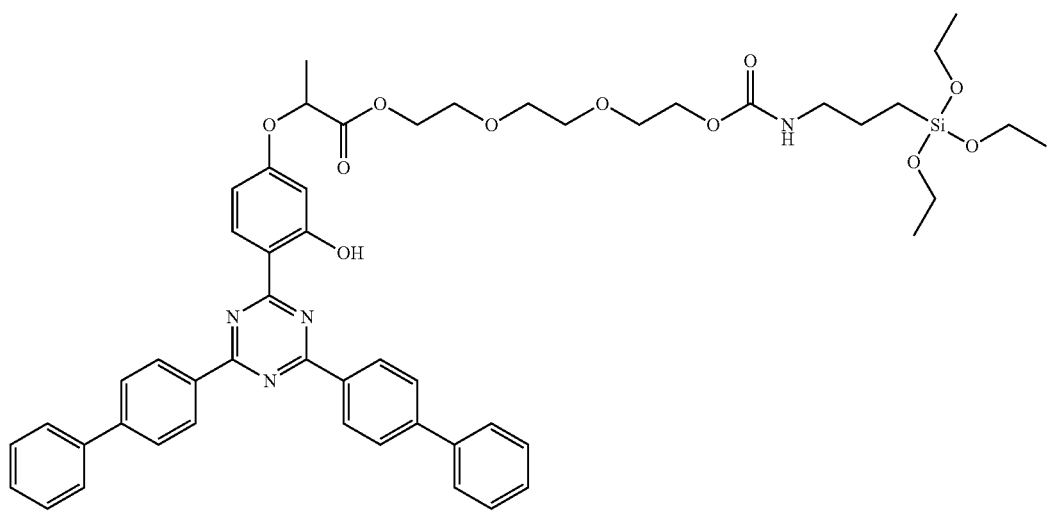
(I.2)
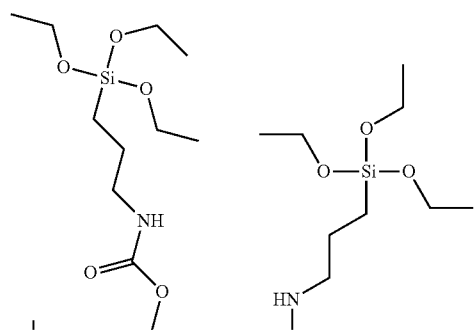
(I.3)

-continued
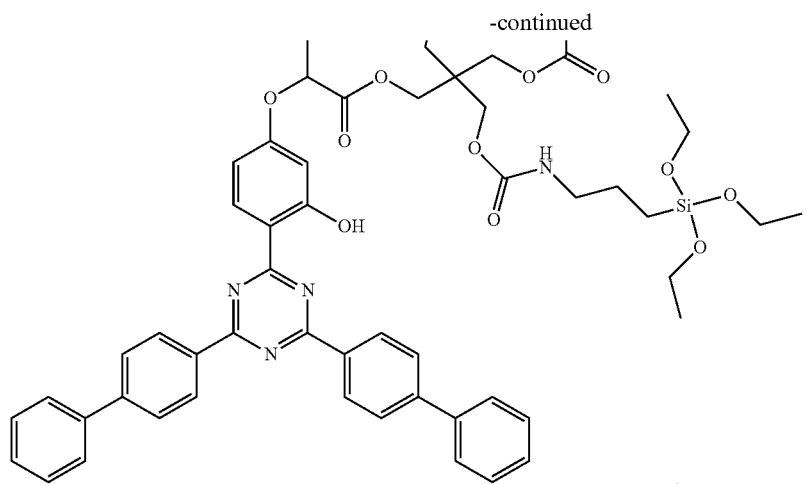
(I.4)
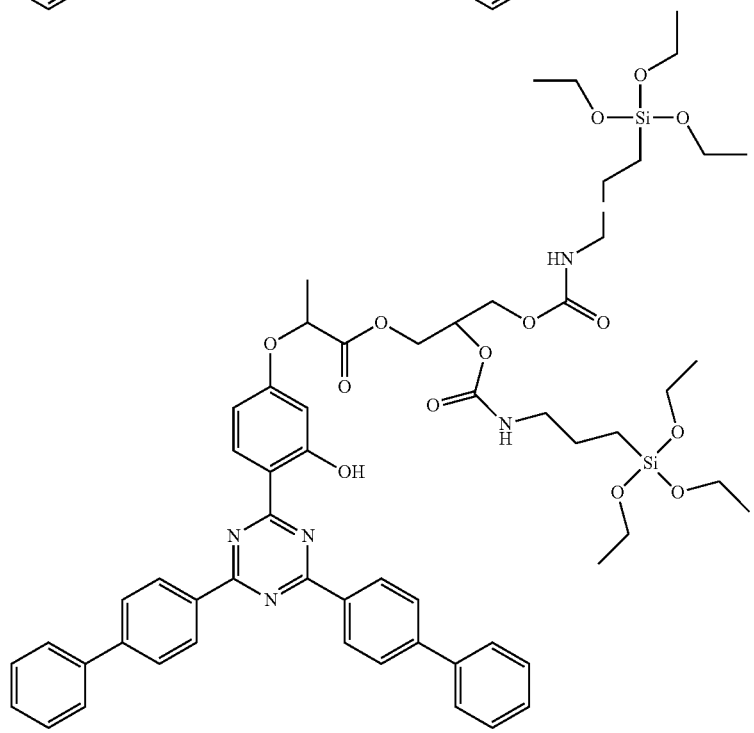
(I.5)
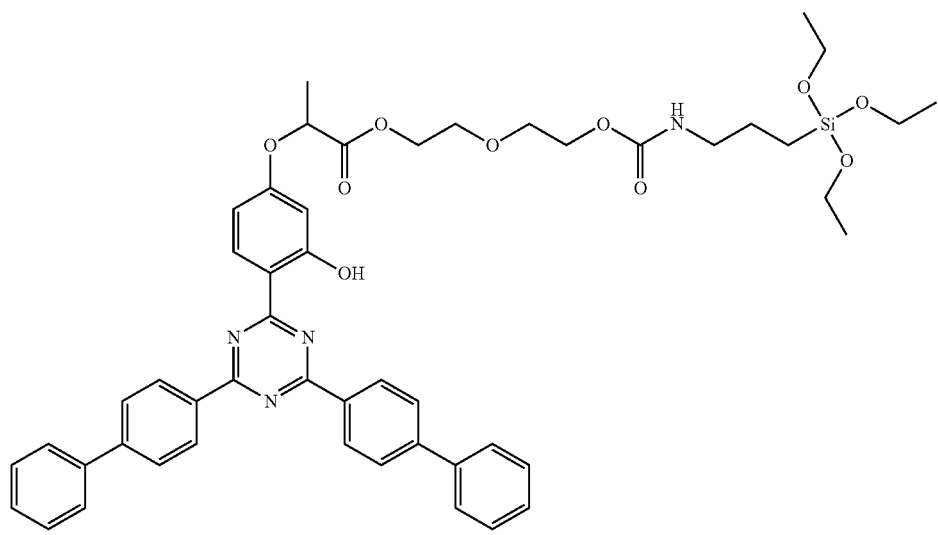

-continued
(I.6)
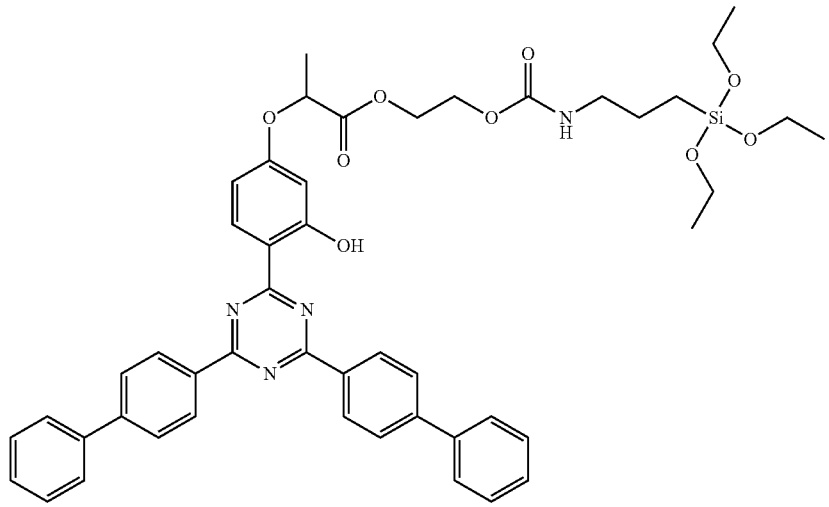
(I.7)
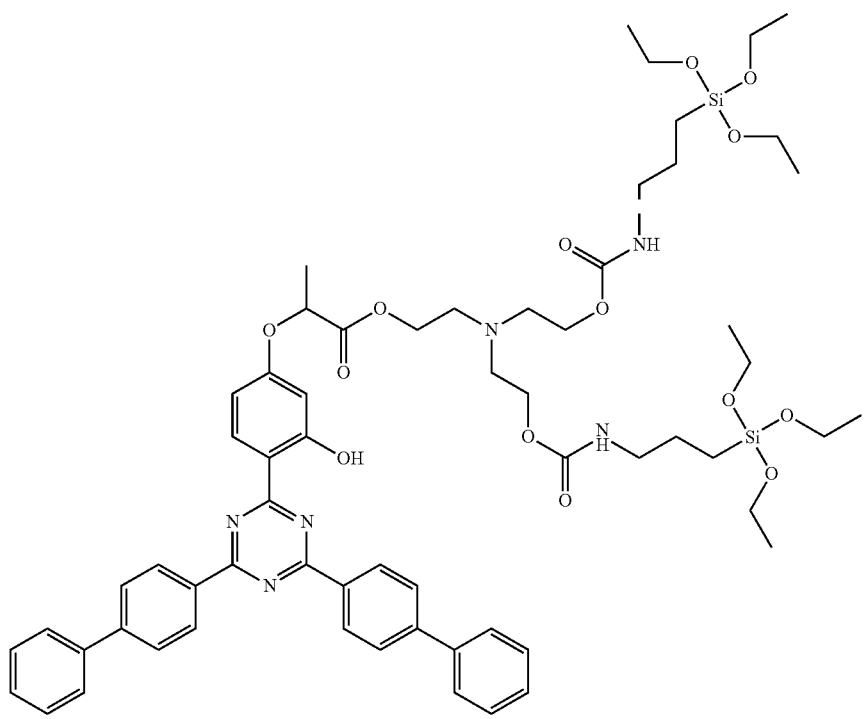
(I.8)
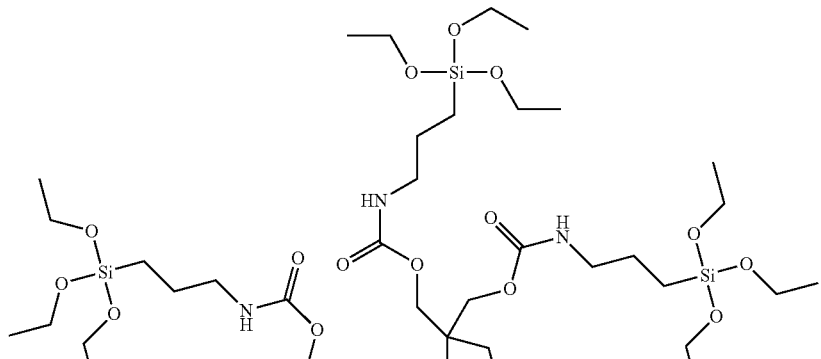

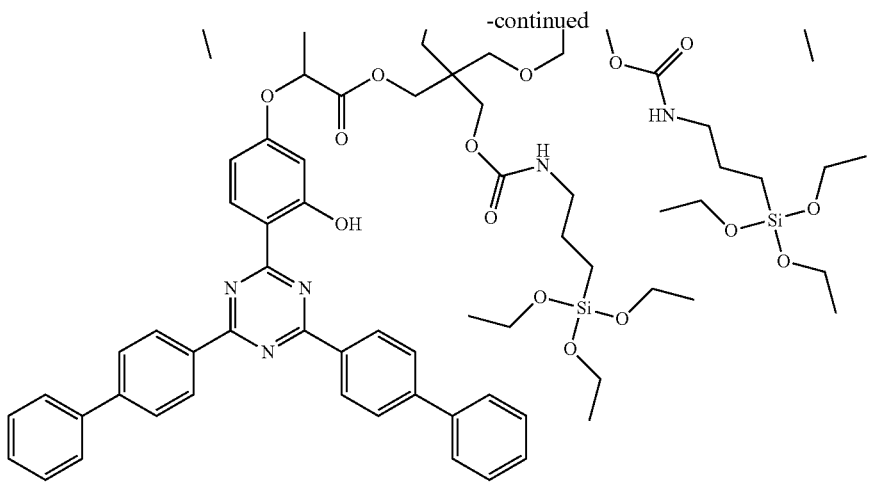

The invention further provides coating compositions which contain the UV-absorbing compounds of the general formula (I), a process for the preparation of the coating compositions, and the use thereof in the coating of surfaces, in particular surfaces of plastics materials.

Preferred coating compositions according to the invention are those based on sol-gel lacquers and other polar hybrid lacquers, because the solubility of the novel UV absorbers is best utilised here. The UV absorbers can, of course, also be used in other lacquer systems, for example in UV-curable acrylate lacquers or UV-curable anhydrous hydrolysable silane systems, as are described, for example, in WO 2008/071363 A or DE-A 2804283.

The novel triazine-based silylated UV absorbers can be introduced into heat-curable sol-gel coating systems in order to obtain scratch-resistant protective layers with high UV protection. No particular requirements are made of the sol-gel coating systems; they can be acidic, basic or neutral. For example, such sol-gel coating solutions can be prepared by hydrolysis of aqueous dispersions of colloidal silicon dioxide and an organoalkoxysilane or mixtures of organoalkoxysilanes of the general formula RSi(OR')$_3$, R in the organoalkoxysilane(s) of the general formula RSi(OR')$_3$ representing a monovalent C1- to C6-alkyl radical or a completely or partially fluorinated C1-C6-alkyl radical, a vinyl or allyl unit, an aryl radical or a C1-C6 alkoxy group. Particularly preferably, R is a C1- to C4-alkyl group, a methyl, ethyl, n-propyl, isopropyl, tert-butyl, sec-butyl or n-butyl group, a vinyl, allyl, phenyl or substituted phenyl unit. The —OR' are selected independently of one another from the group containing C1- to C6-alkoxy groups, a hydroxy group, a formyl unit and an acetyl unit.

The colloidal silicon dioxide is obtainable, for example, as Levasil 200 A (HC Starck), Nalco 1034A (Nalco Chemical Co), Ludox AS-40 or Ludox LS (GRACE Davison). The following compounds may be mentioned as examples of organoalkoxysilanes: 3,3,3-trifluoropropyltrimethoxysilane, methyltrimethoxysilane, methyltrihydroxysilane, methyltriethoxysilane, ethyltrimethoxysilane, methyl-triacetoxysilane, ethyltriethoxysilane, phenyltrialkoxysilane (e.g. phenyltriethoxy-silane and phenyltrimethoxysilane) and mixtures thereof.

Organic and/or inorganic acids or bases, for example, can be used as catalysts.

In an embodiment, the colloidal silicon dioxide particles can also be formed in situ starting from alkoxysilanes by pre-condensation (see in this connection "The Chemistry of Silica", Ralph K. Iler, John Wiley & Sons, (1979), p. 312-461).

The hydrolysis of the sol-gel solution is terminated or slowed considerably by the addition of solvents, preferably alcoholic solvents such as, for example, isopropanol, n-butanol, isobutanol or mixtures thereof. One or more UV absorbers according to the invention, optionally pre-dissolved in a solvent, are then added to the sol-gel coating solution, after which there follows an aging step of a few hours or several days/weeks. Further additives and/or stabilisers such as, for example, flow agents, surface-active additives, thickening agents, pigments, colorings, curing catalysts, IR absorbers, UV absorbers and/or adhesion promoters can further be added. The use of hexamethyldisilazane or comparable compounds, which can lead to reduced susceptibility of the coatings to cracking, is also possible (see also WO 2008/109072 A).

In an embodiment, silylated UV absorbers other than the compounds of formula (I) are additionally present.

The UV absorbers according to the invention can also be mixed with commercially available ready-made sol-gel lacquers in order to increase their UV-protective function. Such lacquers are obtainable, for example, from Momentive Performance Materials under the product names AS4000, AS4700, PHC587 and PHC587B.

The UV-protective formulations according to the invention can be used to produce coatings by applying them to appropriate substrates (B) by conventional methods and then curing them under suitable conditions. Application can be made, for example, by dipping, flooding, spraying, doctor blade application, pouring or brush application; any solvent present is then evaporated off and the coating is cured at room temperature or elevated temperature or by UV light. Details regarding application by conventional methods are to be found, for example, in Organic Coatings: Science and Technology, John Wiley & Sons 1994, Chapter 22, pages 65-82.

The coatings (C) produced from the UV-protective formulations according to the invention offer very good protection of the substrate against UV radiation and provide lasting protection for surfaces against photochemical degradation. They can therefore be used wherever a UV-unstable substrate is to be protected from UV radiation, especially from sunlight or from an artificial radiation source. Many plastics materials, but also natural materials such as wood, can be protected against photochemical degradation in a lasting manner by the coatings according to the invention. The coating of glass, on the other hand, which is likewise possible, does not serve to protect the substrate but to shield against long-wave UV radiation (≥300 nm), which penetrates commercial window glass, for example, almost completely.

Owing to their high transparency, the coatings according to the invention can be used in particular also on transparent plastics materials such as polycarbonate, poly(meth)acrylate, polyester and polystyrene and copolymers and mixtures (blends) thereof. Particularly advantageously, polycarbonates and copolycarbonates, especially bisphenol A-based (aromatic) polycarbonates, are protected against UV radiation. Polycarbonate provided with lasting protection against UV radiation in that manner can then be used, for example, in the glazing of buildings and motor vehicles, where yellowing must be prevented over long periods.

In the case of thermoplastic plastics, it is possible to coat especially extruded as well as injection-moulded moulded bodies, for example in the form of films, coextruded films, sheets, multi-wall sheets and predominantly flat substrates. Fields of application are also to be found in the field of one-component and two-component injection-moulded parts, for example in the form of headlamp cover plates, architectural and automotive glazing.

Depending on the application, the coatings are advantageously applied to one or more sides of the substrates (B). Flat substrates such as films or sheets can accordingly be coated on one side or on two sides.

Preferably, the article consisting of the substrate (B) and coatings (C) can have the structure (B)-(C) or (C)-(B)-(C), where the coatings (C) can be the same or different.

A primer layer (D) can additionally be present between the substrate and the coating. In that case, the preferred structure of the multi-layer article is (B)-(D)-(C), (C)-(B)-(D)-(C) and (C)-(D)-(B)-(D)-C), where the layers (C) and (D), independently of one another, can have the same or different compositions.

The article can additionally contain further coatings. As well as the coatings (C) and (D) there come into consideration as further coatings (E), for example, IR-absorbing layers, IR-reflecting layers, electrically conductive layers, electroluminescent layers, coloured and printed layers for decorative purposes, electrically conductive printed layers, as are used, for example, for automotive window heating, optionally also layers containing heating wires, anti-reflection layers, no-drop coatings, anti-fog coatings, anti-fingerprint coatings and/or combinations thereof. Such coatings can be applied or present as intermediate layers and/or outer layers.

In order to improve the adhesion it is, of course, possible to use a suitable adhesion promoter, which ensures that the coatings according to the invention adhere well to the substrate. The adhesion promoter can be added to the mixture according to the invention or it is applied to the substrate as a separate coating. Conventional adhesion promoters are mostly based on polymethacrylates or polyurethanes. In addition to the adhesion-promoting action, the UV protection of the structure as a whole can optionally be increased by additional UV absorbers and further light stabilisers, preferably HALS. The adhesion promoters or primers can either be baked at elevated temperature after exposure to the air at room temperature (bake-on-bake process) or can be coated directly with the sol-gel solution (wet-on-wet process).

In addition, the coatings obtained from the mixtures according to the invention can be coated with further coatings, which can serve, for example, to improve the mechanical properties (scratch resistance). It is likewise possible to apply a plasma layer, which can provide additional barrier and scratch protection. The plasma layer is applied by the deposition of reactive species according to the prior art—for example plasma enhanced chemical vapour deposition PCVD or magnetron sputtering (e.g. US-A 2007/104956).

The following examples are intended to explain the invention, but without limiting it.

EXAMPLES

Example 1

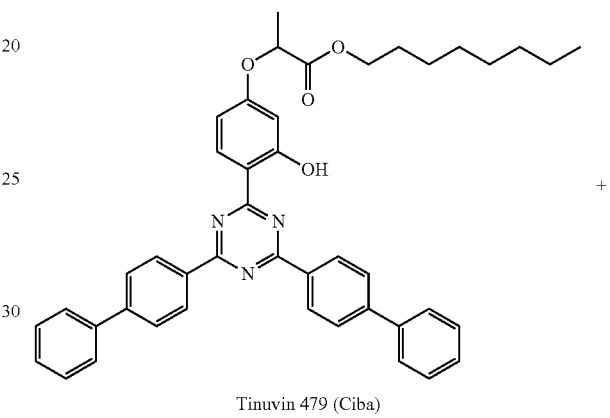

Tinuvin 479 (Ciba)

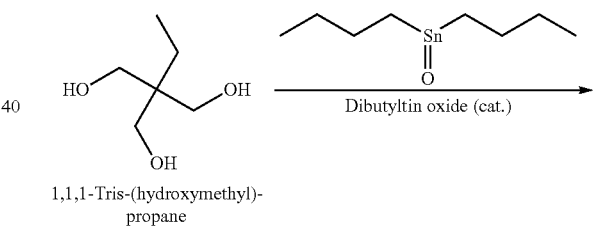

1,1,1-Tris-(hydroxymethyl)-propane

Dibutyltin oxide (cat.)

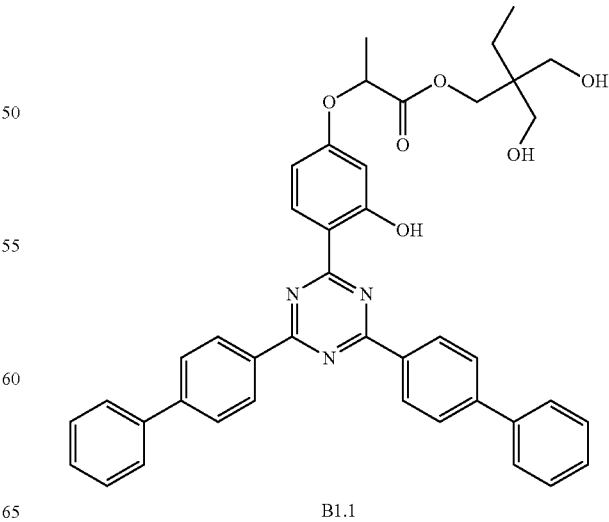

B1.1

110 g of Tinuvin 479 (Ciba Specialty Chemicals Inc., Switzerland) and 8.1 g of dibutyltin oxide (Aldrich) are placed in 217.7 g of 1,1,1-tris-(hydroxymethyl)-propane (Aldrich) and stirred for 5 hours at 165° C. (temperature of the oil bath). The stirred composition is first cloudy and then becomes clear. After cooling of the reaction mixture, the product is precipitated in crystalline form with methanol, filtered off, rinsed with methanol and dried. Further purification is carried out by crystallizing twice from toluene. The melting point of B1.1 is 121.8° C. Yield: 70 g (63% of theory).

Elemental analysis: $C_{42}H_{39}N_3O_6$ (681.80)

calc: C, 73.99; H, 5.77; N, 6.16.

found: C, 74.80; H, 6.00; N, 5.90.

69 g of B1.1 are dissolved in 115 ml of THF; 55.1 g of 3-isocyanatopropyl-triethoxysilane (Aldrich) are added. 0.064 g of dibutyltin didodecanoate (Aldrich) in the form of 26.6 g of THF solution (0.12 g of DBTL in 50 g of THF) is added to the solution, with stirring.

The reaction mixture is stirred for 5 hours under reflux, under argon, and then cooled. The resulting solution is added dropwise to 1100 ml of hexane, with stirring. A thick suspension forms; the product is filtered off and stirred again for one hour in 1000 ml of hexane. After filtration, the product, compound I.1, is dried in vacuo. The melting point is 87.4° C. Yield: 100 g (84% of theory).

Elemental analysis: $C_{62}H_{81}N_5O_{14}Si_2$ (1176.53)

calc: C, 63.30; H, 6.94; N, 5.95.

found: C, 63.10; H, 7.10; N, 5.80.

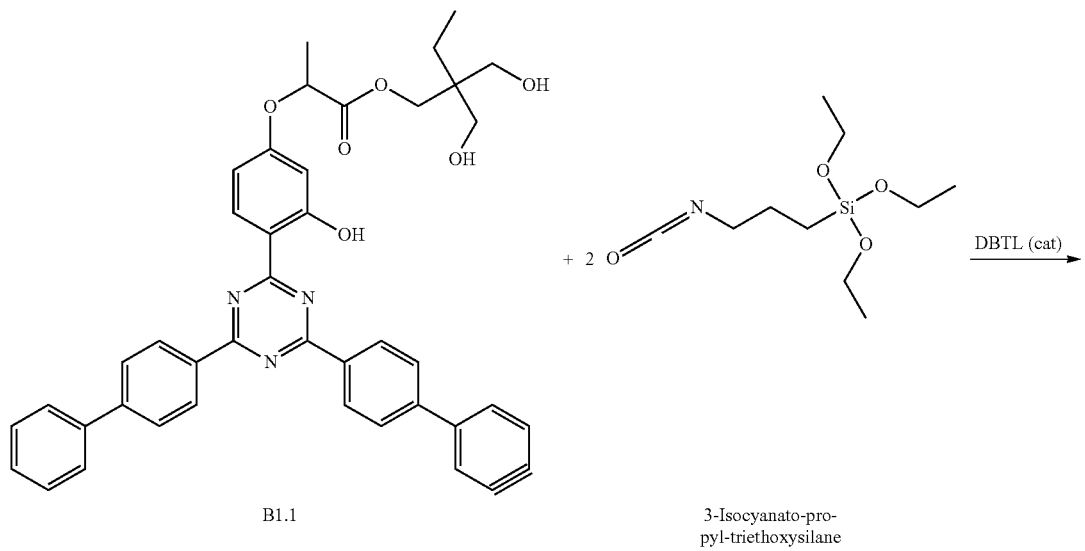

B1.1

3-Isocyanato-propyl-triethoxysilane

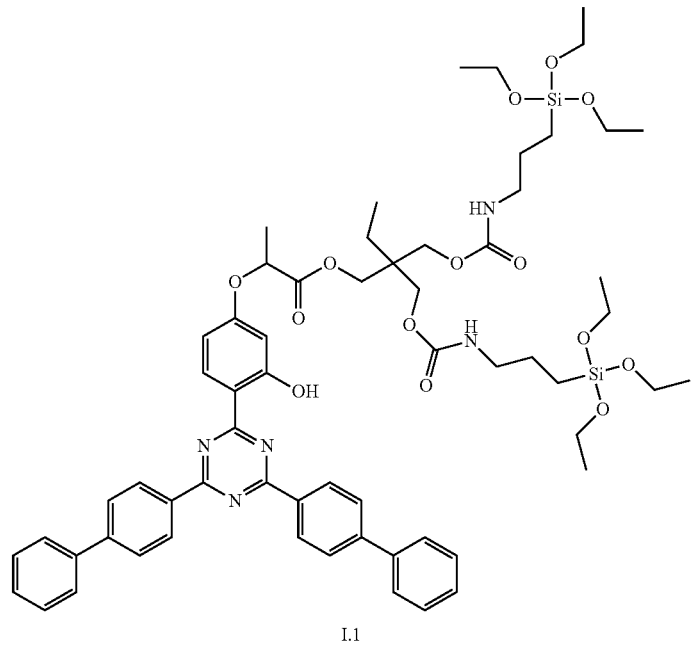

I.1

17
Example 2
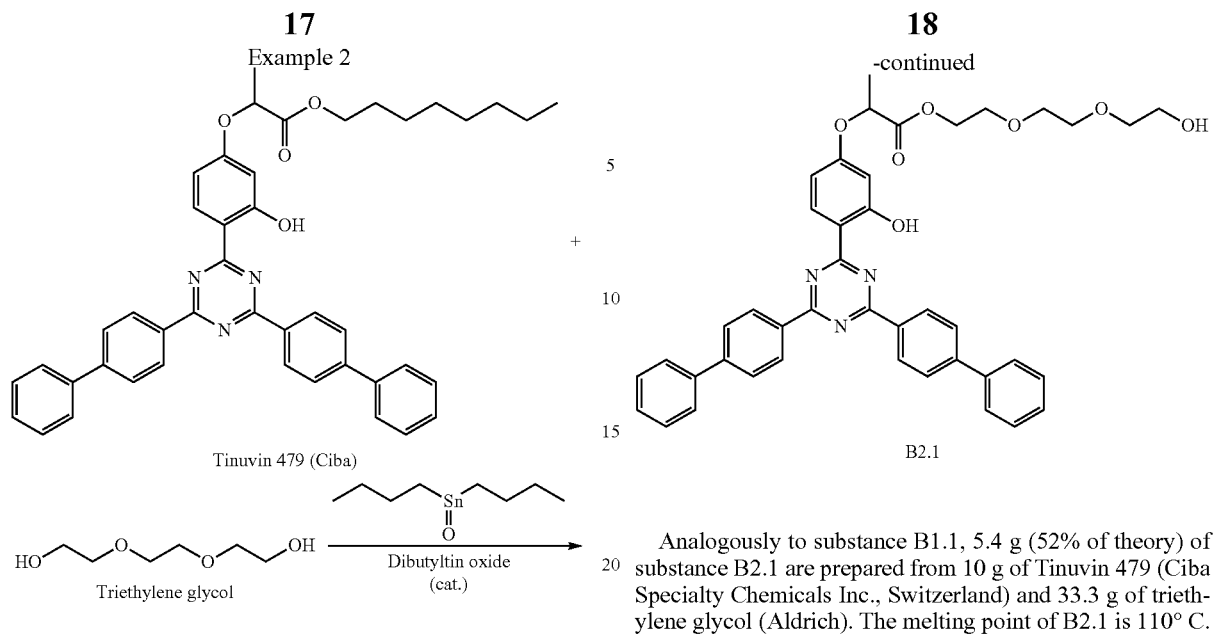
Tinuvin 479 (Ciba)
18
-continued
B2.1
Analogously to substance B1.1, 5.4 g (52% of theory) of substance B2.1 are prepared from 10 g of Tinuvin 479 (Ciba Specialty Chemicals Inc., Switzerland) and 33.3 g of triethylene glycol (Aldrich). The melting point of B2.1 is 110° C.
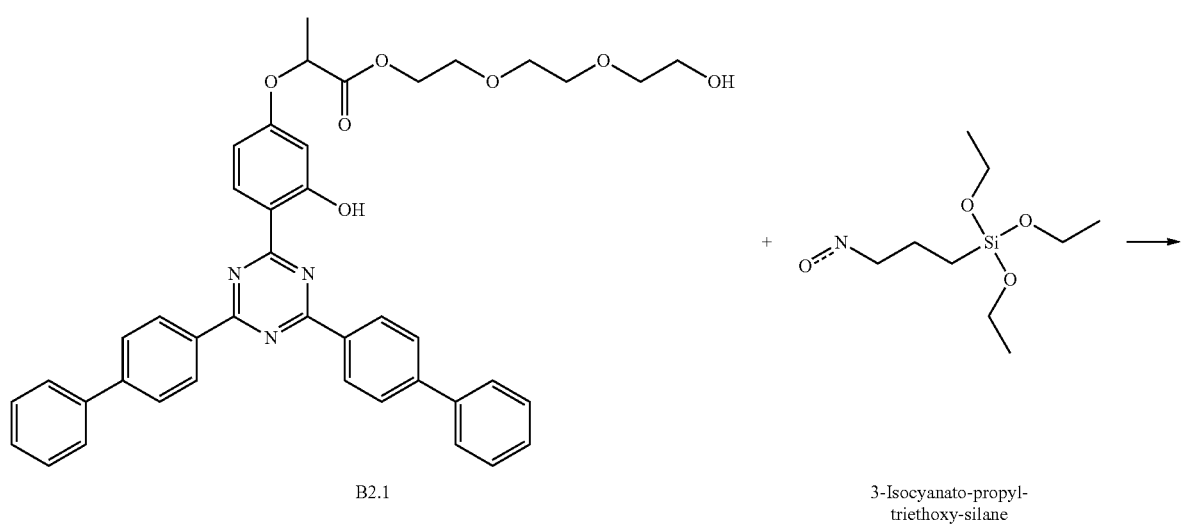
B2.1
3-Isocyanato-propyl-triethoxy-silane
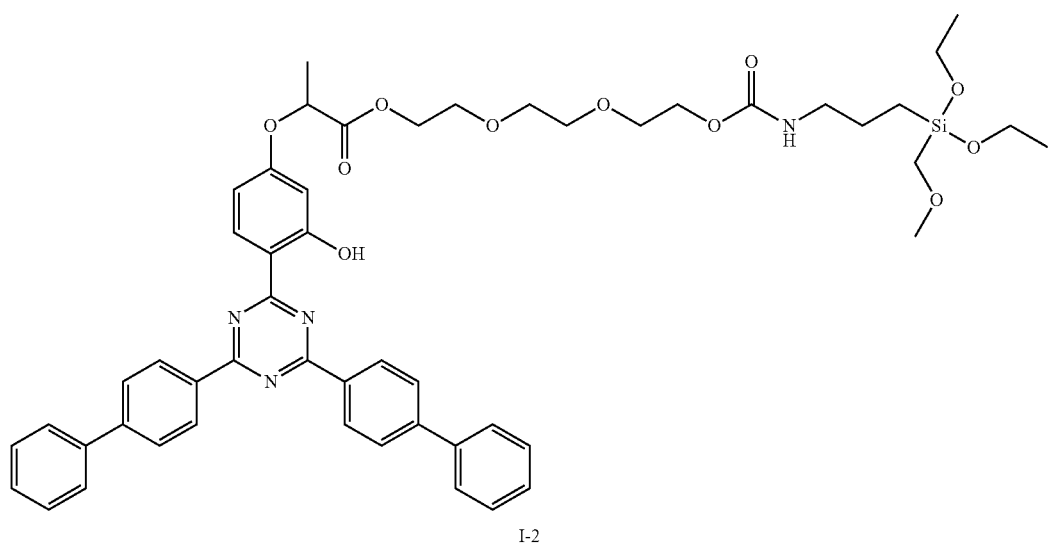
I-2

Analogously to substance I.1, 6.0 g (88% of theory) of substance I.2 are prepared from 5 g of B2.1 and 1.77 g of 3-isocyanatopropyl-triethoxysilane (Aldrich). The melting point of substance I.2 is 80° C.

Elemental analysis: $C_{52}H_{60}N_4O_{11}Si$ (945.16)

calc: C, 66.08; H, 6.40; N, 5.93.

found: C, 65.10; H, 6.70; N, 5.70.

Example 3

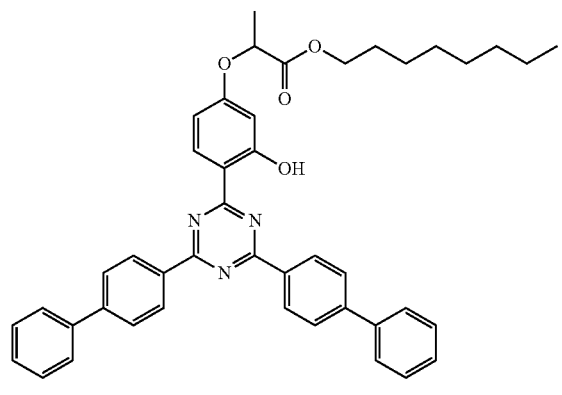

Tinuvin 479

+

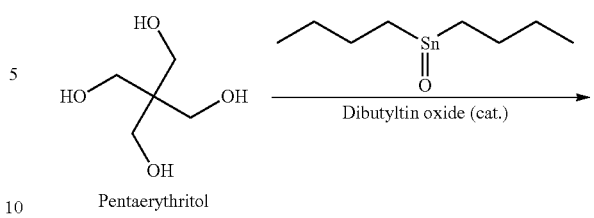
Pentaerythritol

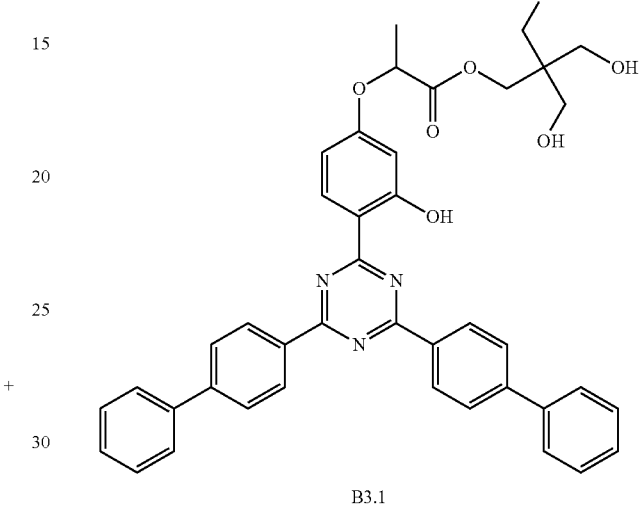

B3.1

Analogously to substance B1.1, 32.8 g (41% of theory) of substance B3.1 are prepared from 80 g of Tinuvin 479 (Ciba Specialty Chemicals Inc., Switzerland), dissolved in 250 g of 1,3-dimethyl-3,4,5,6-tetrahydro-2-pyrimidone (Aldrich), and 120 g of pentaerythritol (Aldrich).

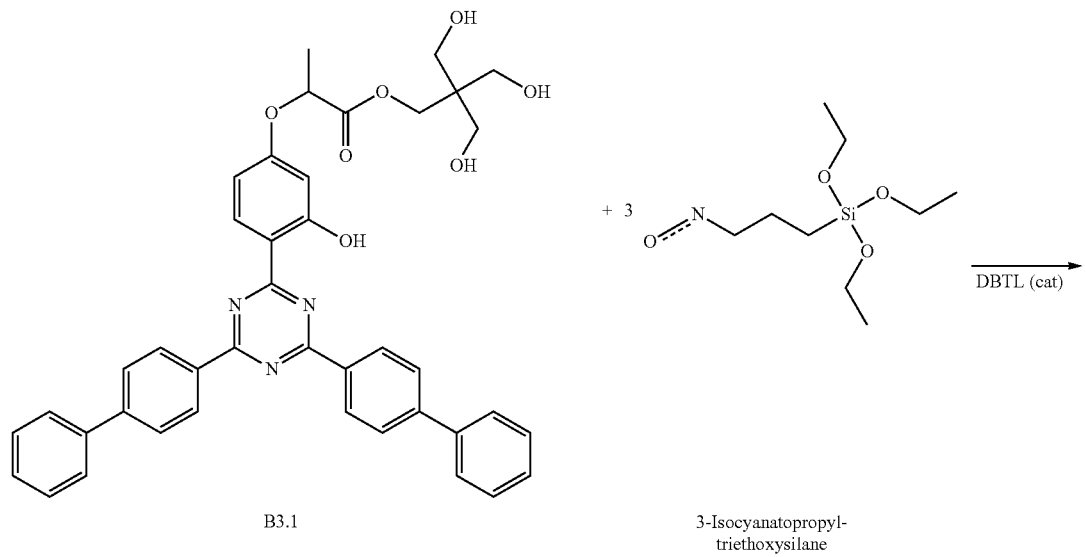

B3.1

3-Isocyanatopropyl-triethoxysilane

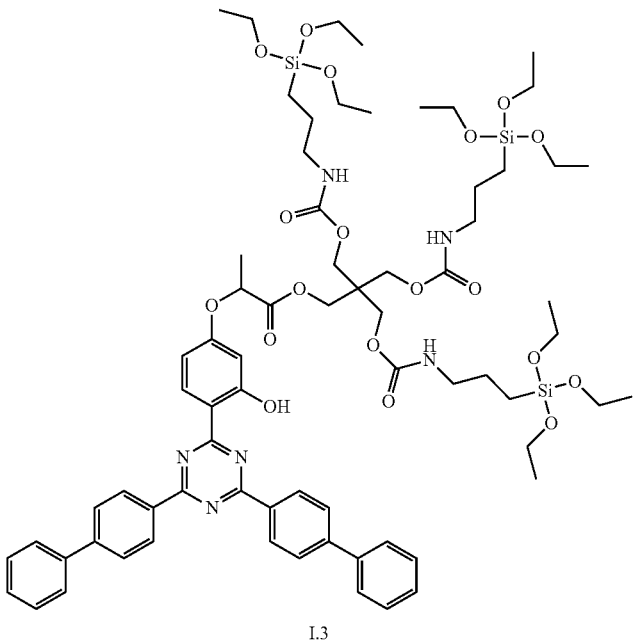

I.3

Analogously to substance I.1, 42 g (56% of theory) of substance I.3 are prepared from 36 g of B3.1 and 86.3 g of 3-isocyanatopropyl-triethoxysilane. The melting point is 127° C.

Elemental analysis: $C_{71}H_{100}N_6O_{19}Si_3$ (1425.88)

calc: C, 59.81; H, 7.07; N, 5.89.

found: C, 59.90; H, 7.00; N, 5.90.

Examples 4-10

Production of the Coated Polycarbonate Sheets a) Preparation of the Sol-Gel (without UV Absorber)

A suspension consisting of 41.83 g of colloidal silicon dioxide (Levasil 200A from HC Starck (Germany), 30% in water, pH 9.5, average particle size 15 nm) and 13.8 g of distilled water is added to a mixture of 57.67 g of methyltrimethoxysilane from ABCR, Germany, and 0.42 g of acetic acid. Stirring is carried out for 16-18 hours at room temperature. The mixture is then diluted with 61.7 g of isopropanol and 61.7 g of n-butanol.

b) Preparation of the Coatings Containing UV Absorber 0.16 g (0.8 wt. %) of the UV absorbers listed in Table 1 is added to in each case 19.84 g of the stock solution. Stirring is carried out for 2 hours, the pH value is increased to 7.5 with ammonia, and filtration is carried out over a pressure suction filter (2-4 µm cellulose filter).

c) Application:

Optical grade injection-moulded polycarbonate (PC) sheets of Makrolon® 2808 (Bayer MaterialScience AG; medium-viscosity bisphenol A polycarbonate, MVR 10 g/10 min according to ISO 1133 at 300° C. and 1.2 kg, without UV stabilisation) having a size of 10×15×0.32 cm are tempered for one hour at 120° C., rinsed with isopropanol and exposed to the air. The sheets are then coated with a commercially available PMMA primer (primer SHP 401 from Momentive Performance Materials), exposed to the air for 30 minutes at room temperature and then flood-coated directly with the respective freshly filtered UV-absorber-containing sol-gel suspension by the wet-on-wet process. After being exposed to the air for 30 minutes at room temperature, the sheets are cured for one hour at 120° C.

As an indication of the solubility/compatibility of the UV absorber in the sol-gel suspension, the initial haze values of the individual PC sheets coated with UV-absorber-containing sol-gel are determined according to ASTM D 1003 using a Haze Gard Plus from Byk-Gardner. Poorly soluble UV absorbers exhibit higher haze than readily soluble ones.

TABLE 1

Layer thickness and haze measurements on PC sheets with the UV-absorber-containing sol-gel coatings of Examples 4-10

| | UV absorber used |
|---|---|
| Example 4 (comparison) | 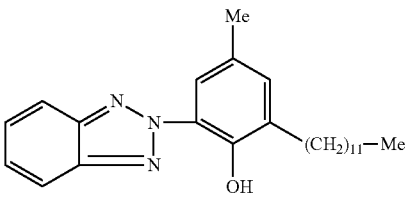<br>Tinuvin 171 (Ciba Speciality Chemicals)<br>2-(2-Hydroxy-3-dodecyl-5-methylphenyl)benzotriazole<br>CAS No. 125304-04-3<br>Layer thickness (μm): 2.5-4.8<br>Initial haze (%): 29-50 |
| Example 5 (comparison) | 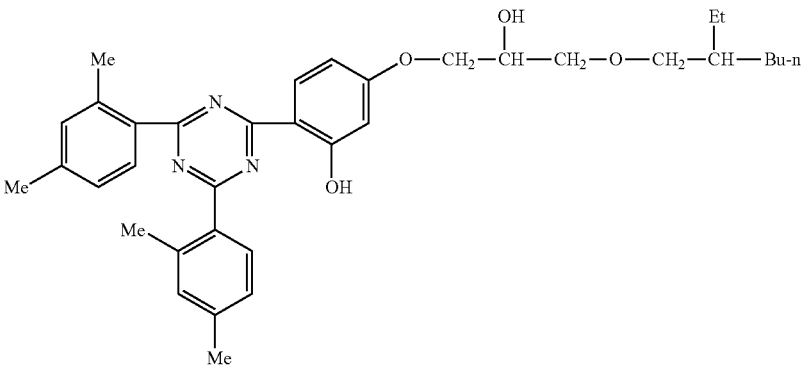<br>Tinuvin 405 (Ciba Speciality Chemicals)<br>2-[2-Hydroxy-4-[3-(2-ethylhexyl-1-oxy)-2-hydroxypropyloxy]phenyl]-<br>4,6-bis(2,4-dimethylphenyl)-1,3,5-triazine<br>CAS No. 137658-79-8<br>Layer thickness (μm): 2.5-4.5<br>Initial haze (%): 22-41 |
| Example 6 (comparison) | 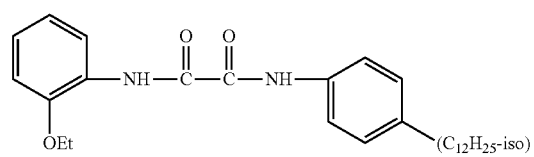<br>Sanduvor 3206 (Clariant)<br>N-(2-Ethoxyphenyl)-N'-(p-isododecylphenyl)oxamide<br>CAS No. 82493-14-9<br>Layer thickness (μm): 2.3-4.4<br>Initial haze (%): 5.7-17 |
| Example 8 (according to the invention) | Compound I.2<br>Layer thickness (μm): 2.0-3.9<br>Initial haze (%): 0.2-0.3 |
| Example 9 (according to the invention) | Compound I.1<br>Layer thickness (μm): 2.5-4.8<br>Initial haze (%): 0.6-1.7 |
| Example 10 (according to the invention) | Compound I.3<br>Layer thickness (μ.m): 2.5-4.4<br>Initial haze (%): 3.8-6.7 |

Example 11

According to the Invention 0.2 g of compound I.1 is added to 20 g of lacquer AS4000 (Momentive Performance Materials) and stirred for one hour at room temperature. The solid substance dissolves completely. The resulting sol-gel suspension containing 1 wt. % of compound I.1 is filtered (membrane filter of pore size 0.2 μm), applied to a PC sheet of Makrolon® 2808, primed with primer SHP 401 from Momentive Performance Materials, according to Example 4c) and heat cured. A highly transparent coating from 5 to 8 μm thick having an initial haze of 0.38% is obtained.

Example 12

According to the Invention 1.0 g of compound I.1 is added to 20 g of lacquer AS4000 (Momentive Performance Materials) and stirred for one hour at room temperature. The solid substance dissolves completely. The resulting sol-gel suspension containing about 5 wt. % of compound I.1 is filtered (membrane filter of pore size 0.2 μm), applied to a PC sheet of Makrolon® 2808, primed with primer SHP 401 from Momentive Performance Materials, according to Example 4c) and heat cured. A highly transparent coating from 6 to 9 μm thick having an initial haze of 0.36% is obtained.

Example 13

According to the Invention 0.2 g of compound I.1 is added to 20 g of lacquer PHC587 (Momentive Performance Materials) and stirred for one hour at room temperature. The solid substance dissolves completely. The resulting sol-gel suspension containing 1 wt. % of compound I.1 is filtered (membrane filter of pore size 0.2 μm), applied to a PC sheet of Makrolon® 2808 according to Example 4c) and heat cured. A highly transparent coating from 6 to 10 μm thick having an initial haze of 0.32% is obtained.

Example 14

According to the Invention 1.0 g of compound I.1 is added to 20 g of lacquer PHC587 (Momentive Performance Materials) and stirred for one hour at room temperature. The solid substance dissolves completely. The resulting sol-gel suspension containing about 5 wt. % of compound I.1 is filtered (membrane filter of pore size 0.2 μm), applied to a PC sheet of Makrolon® 2808 according to Example 4c) and heat cured. A highly transparent coating from 5 to 7 μm thick having an initial haze of 0.45% is obtained.

Example 15

Comparison 0.2 g of Tinuvin 479 is added to 20 g of lacquer PHC587 (Momentive Performance Materials) and stirred for 2 hours at room temperature. The substance does not dissolve and is largely removed from the lacquer by distillation. Owing to the insolubility of the UV absorber, it was not possible to produce a corresponding UV-absorber-containing lacquer or a sheet coated therewith.

The invention claimed is:

1. A coating composition comprising a lacquer and an UV-absorbing compound which is soluble in polar media and having the formula (I)

$$A-X(-T-Q-P)_n \qquad (I),$$

wherein
A represents

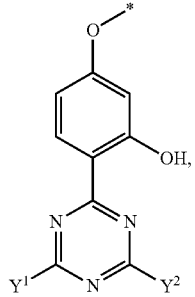

wherein
$Y^1$ and $Y^2$, independently of one another, represent substituents having the formula

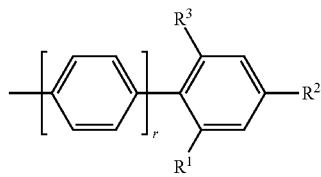

wherein
r is 0 or 1,
$R^1$, $R^2$, and $R^3$, independently of one another, represent H, OH, C1-20 alkyl, C4-12 cycloalkyl, C2-20 alkenyl, C1-20 alkoxy, C4-12 cycloalkoxy, C2-20 alkenyloxy, C7-20 aralkyl, halogen, —C≡N, C1-5 haloalkyl, —SO2R', —SO3H, —SO3M (M=alkali metal), —COOR', —CONHR', —CONR'R", —OCOOR', —OCOR', —OCONHR', (meth)acrylamino, (meth)acryloxy, C6-12 aryl (optionally substituted by C1-12 alkyl, C1-12 alkoxy, CN and/or by halogen), or C3-12 heteroaryl (optionally substituted by C1-12 alkyl, C1-12 alkoxy, CN and/or by halogen) and wherein
R' and R" represent —H, C1-20 alkyl, —C4-12 cycloalkyl, C6-12 aryl (optionally substituted by C1-12 alkyl, C1-12 alkoxy, CN and/or by halogen) or C3-12 heteroaryl (optionally substituted by C1-12 alkyl, C1-12 alkoxy, CN and/or by halogen),
X represents a linear or branched linker, wherein between the O atom of group A and each T group there is a chain of at least 4 atoms selected from the group consisting of carbon, oxygen, nitrogen, sulfur, phosphorus and silicon in the chain,
T represents a urethane group —O—(C═O)—NH— or a urea group —NH—(C═O)—NH—,
Q represents —(CH$_2$)$_m$—, wherein m is 1,2 or 3,
P represents a mono-, di- or tri-alkoxysilane group, and
n represents an integer from 1 to 5,
wherein the lacquer is a hybrid lacquer obtained by a sol-gel process.

2. The coating composition according to claim 1, wherein the coating composition further comprises one or more further additives selected from the group consisting of stabilisers, flow agents, surface-active additives, pigments, colourings, curing catalysts, IR absorbers and UV absorbers other than the compounds of formula (I) and adhesion promoters.

3. The coating composition according to claim 1, wherein the coating composition further comprises a silylated UV absorber other than the compounds of formula (I).

4. A method for coating a substrate comprising
a) applying a layer of the coating composition according to claim 1 to a substrate,
b) optionally removing any solvent present, and
c) curing the applied layer.

5. The coating composition according to claim 1, wherein the UV absorbing compound comprises a compound having the formula (I.1) to (I.8):

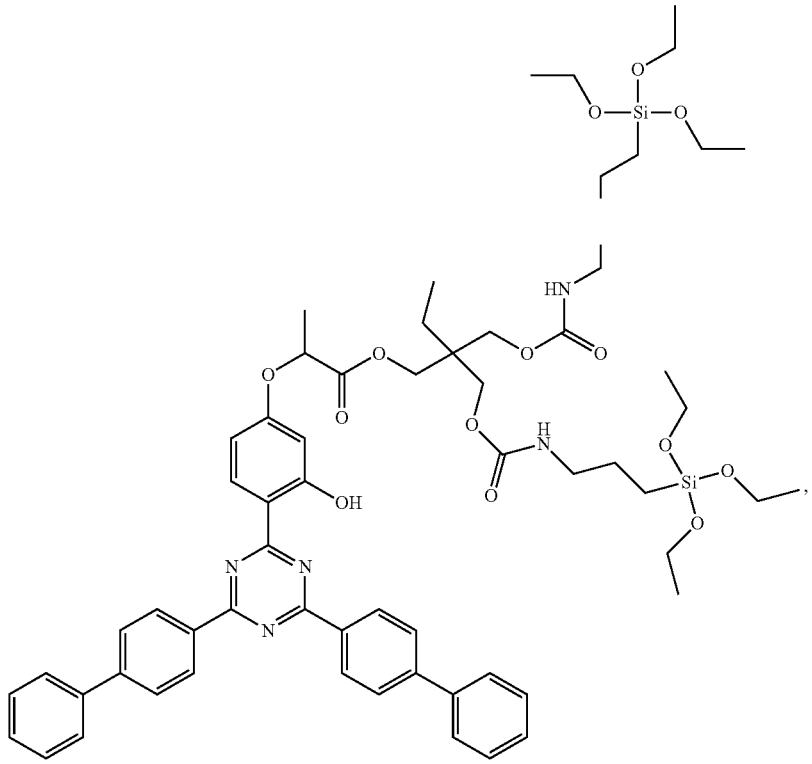

(I.1)

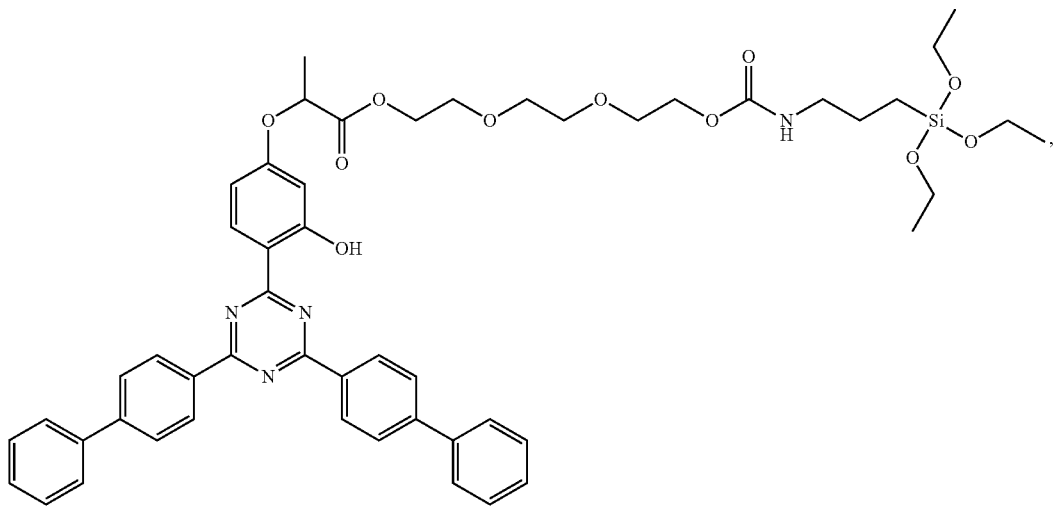

(I.2)

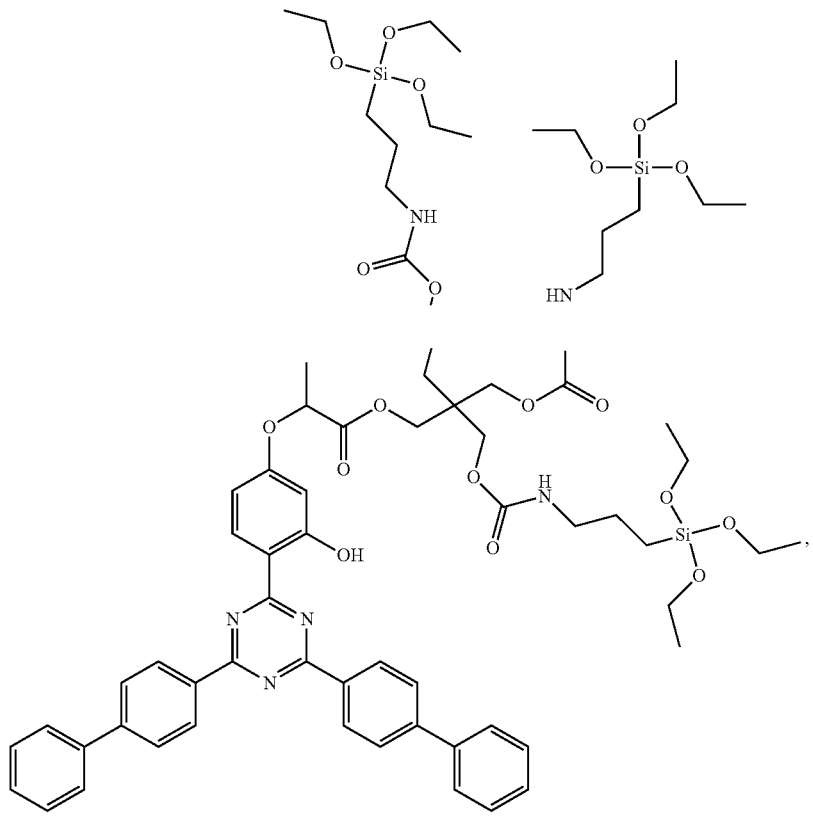
(I.3)
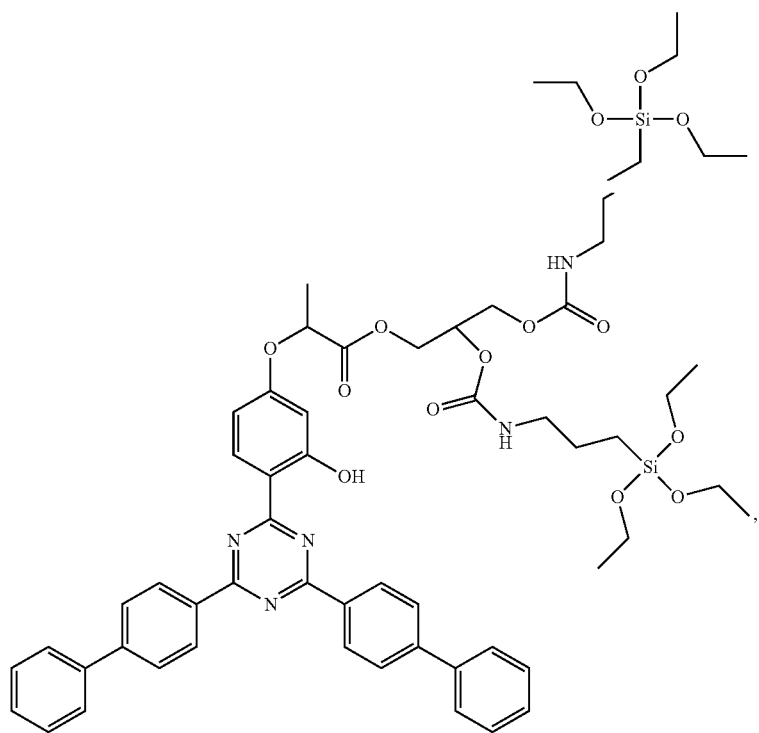
(I.4)

-continued
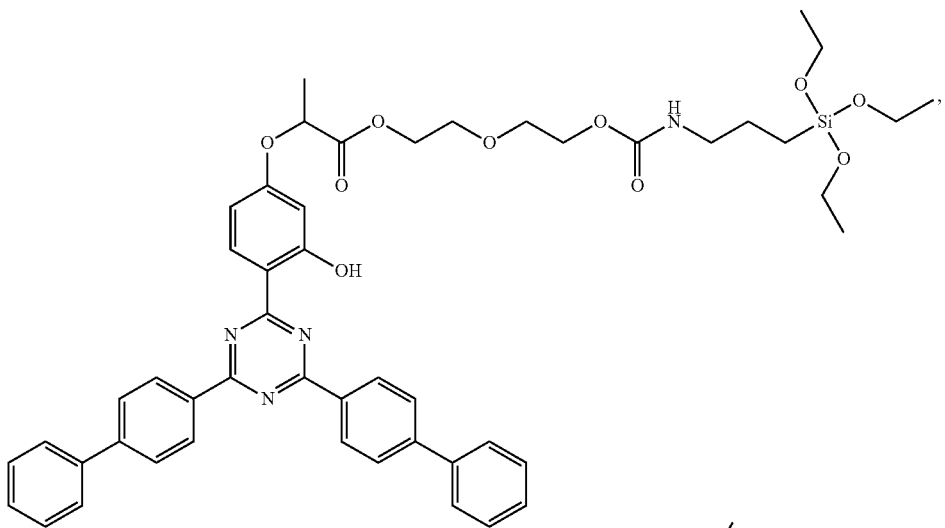
(I.5)
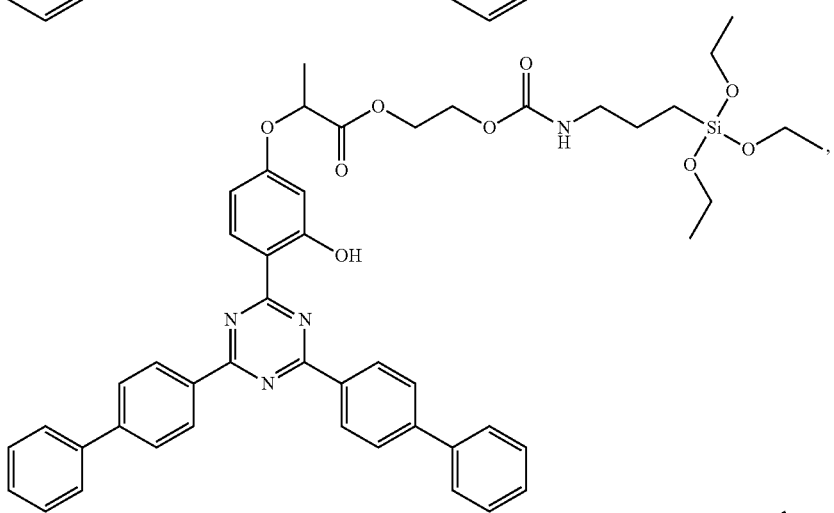
(I.6)
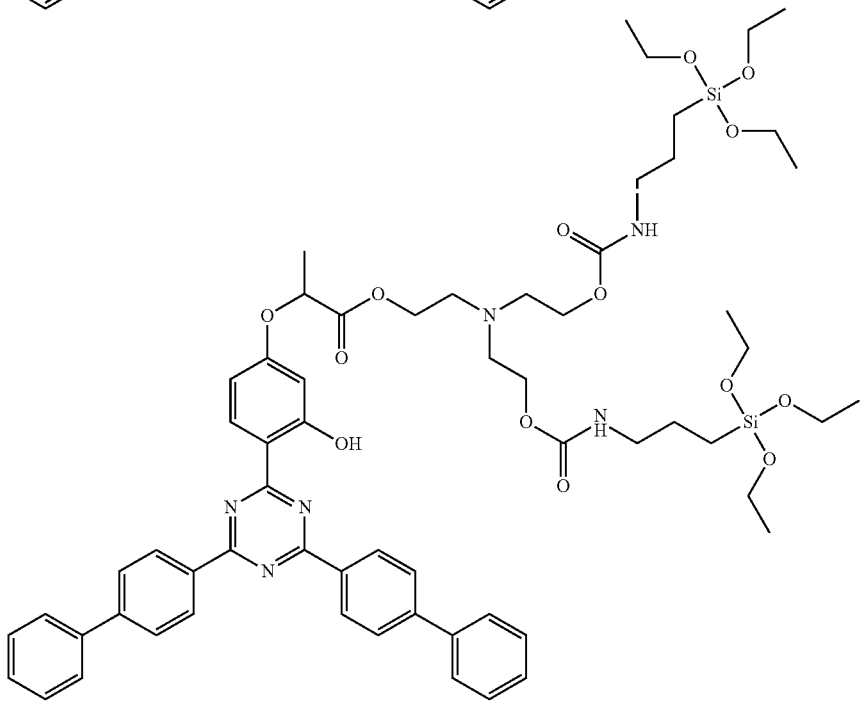
(I.7)

(I.8)

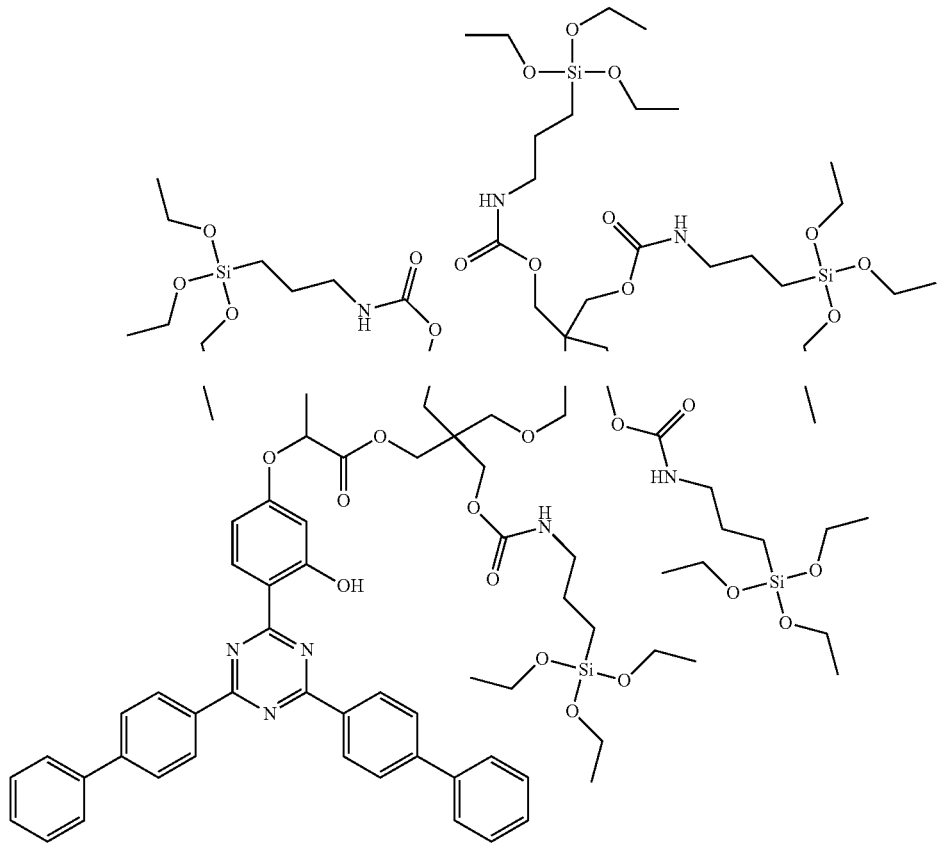

6. The coating composition according to claim 1, wherein P represents a mono-, di- or tri-alkoxysilane group and wherein alkoxy represents methoxy, ethoxy or (2-methoxy)-ethoxy.

7. The coating composition according to claim 1, wherein r is 1.

8. An article comprising a substrate and one or more coatings comprising the coating composition according to claim 1.

9. The article according to claim 8, further comprising one or more further coatings.

10. The article according to claim 9, wherein one of the one or more further coatings is a primer coating.

11. The article according to claim 8, wherein the substrate is a molded body or extrudate of one or more thermoplastics.

12. The article according to claim 11, wherein the one or more thermoplastics comprise polycarbonates and/or copolycarbonates.

13. The article according to claim 8, wherein the article is a film, coextruded film, sheet, multi-wall sheet, headlamp cover plate, automotive glazing or architectural glazing.

14. A coating composition comprising a lacquer and an UV-absorbing compound which is soluble in polar media and having the formula (I)

$$A\text{-}X(\text{-}T\text{-}Q\text{-}P)_n \qquad (I),$$

wherein
A represents

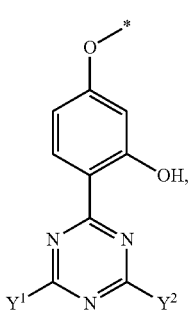

wherein
$Y^1$ and $Y^2$, independently of one another, represent substituents having the formula

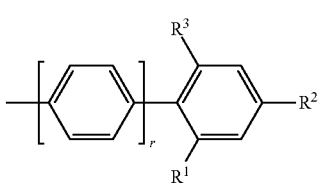

wherein r is 0 or 1,

R¹, R², and R³, independently of one another, represent H, OH, C1-20 alkyl, C4-12 cycloalkyl, C2-20 alkenyl, C1-20 alkoxy, C4-12 cycloalkoxy, C2-20 alkenyloxy, C7-20 aralkyl, halogen, —C≡N, C1-5 haloalkyl, —SO2R', —SO3H, —SO3M (M=alkali metal), —COOR', —CONHR', —CONR'R", —OCOOR', —OCOR', —OCONHR', (meth)acrylamino, (meth)acryloxy, C6-12 aryl (optionally substituted by C1-12 alkyl, C1-12 alkoxy, CN and/or by halogen), or C3-12 heteroaryl (optionally substituted by C1-12 alkyl, C1-12 alkoxy, CN and/or by halogen)

and wherein

R' and R" represent —H, C1-20 alkyl, —C4-12 cycloalkyl, C6-12 aryl (optionally substituted by C1-12 alkyl, C1-12 alkoxy, CN and/or by halogen) or C3-12 heteroaryl (optionally substituted by C1-12 alkyl, C1-12 alkoxy, CN and/or by halogen), X represents a linear or branched linker, wherein between the O atom of group A and each T group there is a chain of at least 4 atoms selected from the group consisting of carbon, oxygen, nitrogen, sulfur, phosphorus and silicon in the chain, T represents a urethane group —O—(C=O)—NH— or a urea group —NH—(C=O)—NH—, Q represents —(CH₂)ₘ—, wherein m is 1,2 or 3, P represents a mono-, di- or tri-alkoxysilane group, and n represents an integer from 1 to 5, wherein the lacquer is a sol-gel lacquer.

15. The coating composition according to claim 14, wherein the coating composition further comprises one or more further additives selected from the group consisting of stabilisers, flow agents, surface-active additives, pigments, colourings, curing catalysts, IR absorbers and UV absorbers other than the compounds of formula (I) and adhesion promoters.

16. The coating composition according to claim 14, wherein the coating composition further comprises a silylated UV absorber other than the compounds of formula (I).

17. The coating composition according to claim 14, wherein the UV absorbing compound comprises a compound having the formula (I.1) to (I.8):

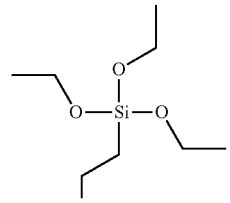

(I.1)

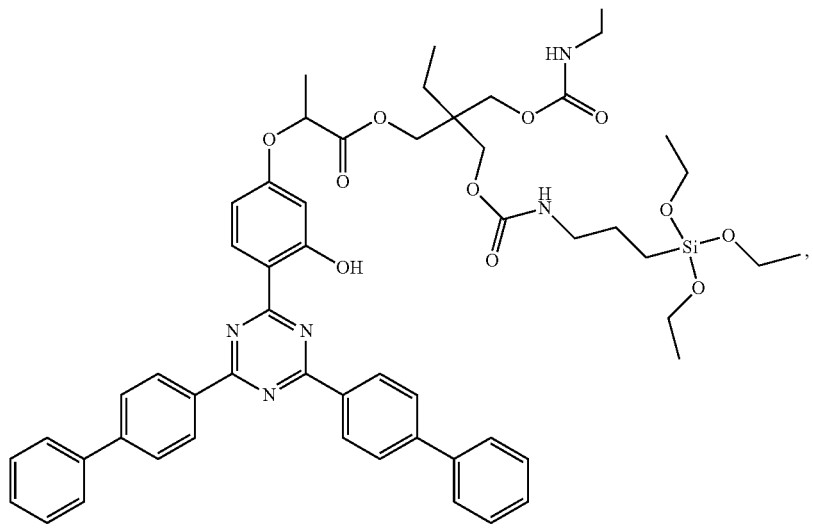

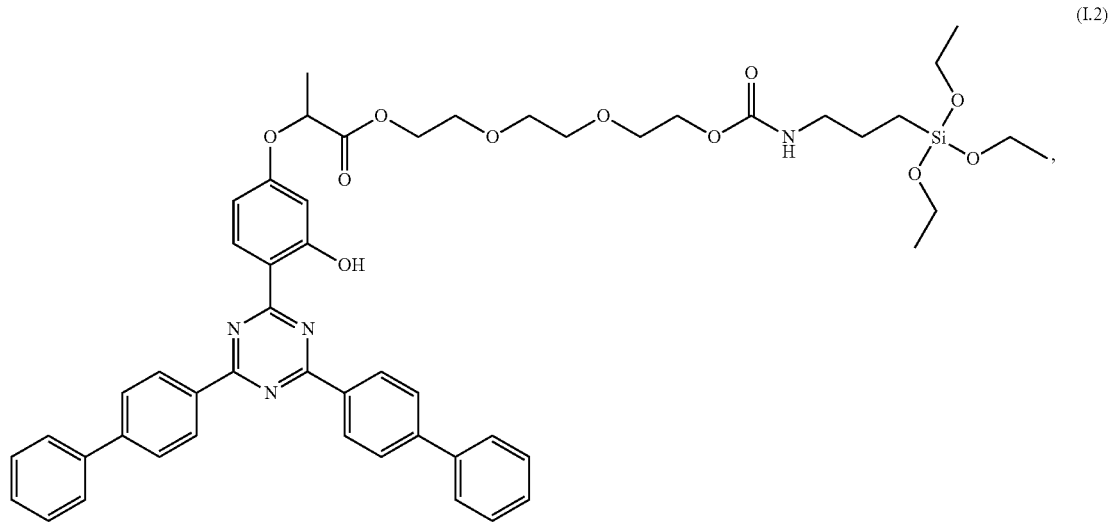
(I.2)
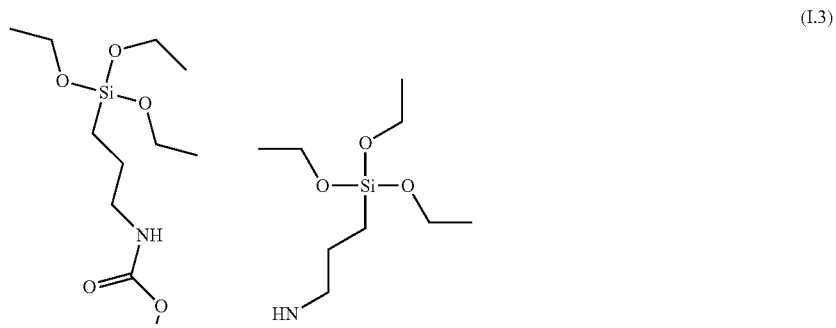
(I.3)
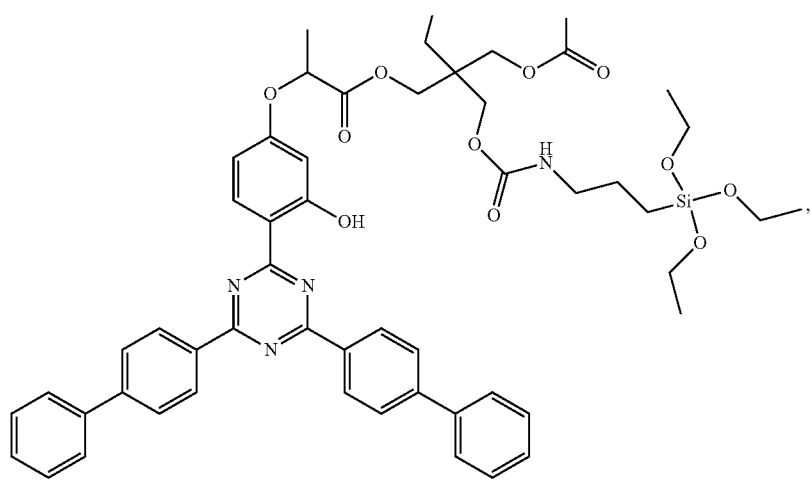
(I.4)
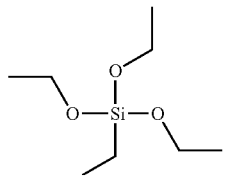

-continued
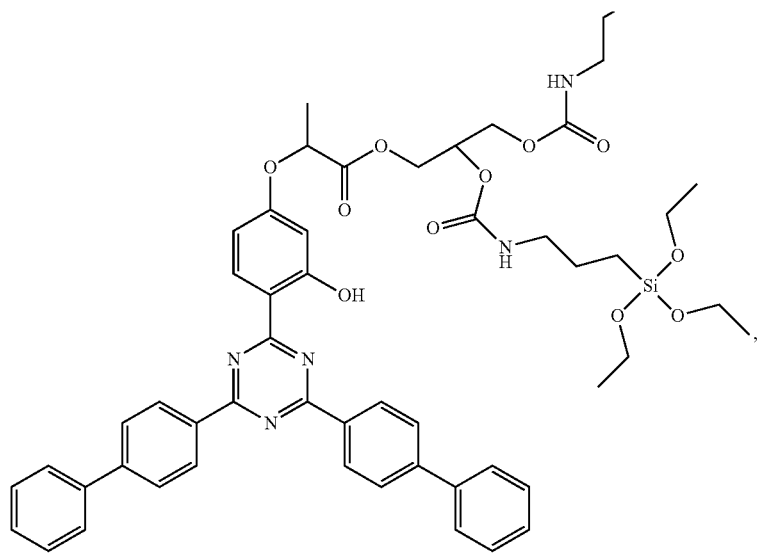
(I.5)
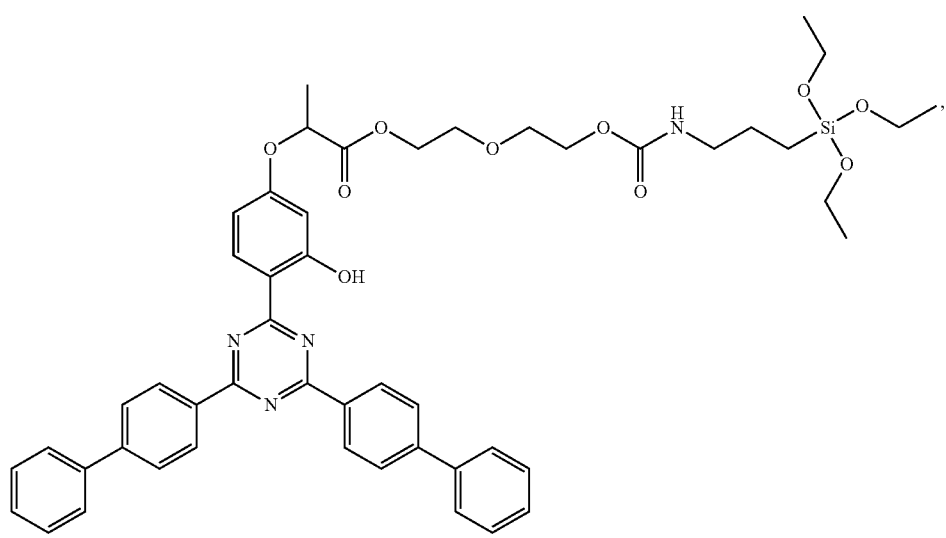
(I.6)
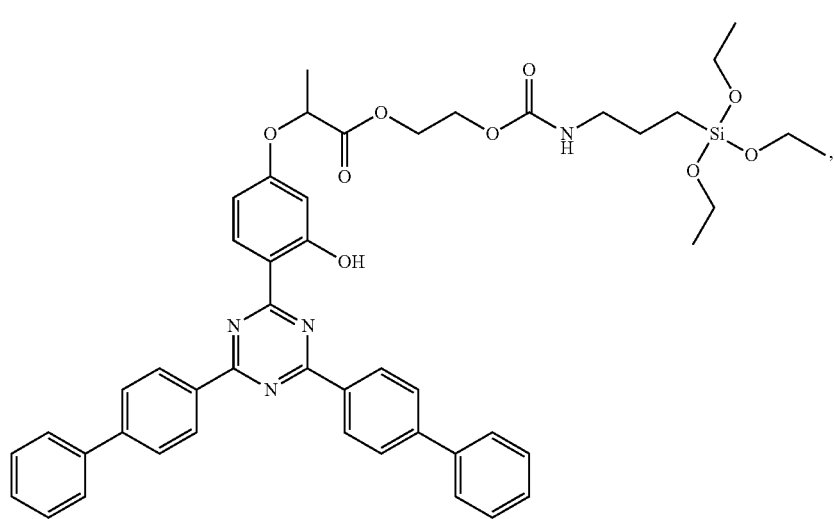

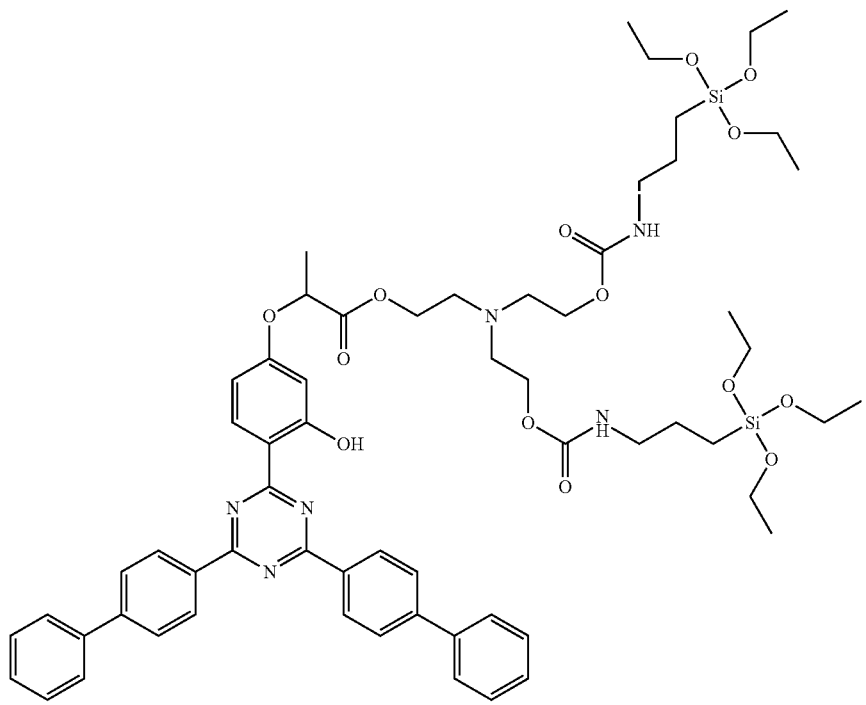
(I.7)
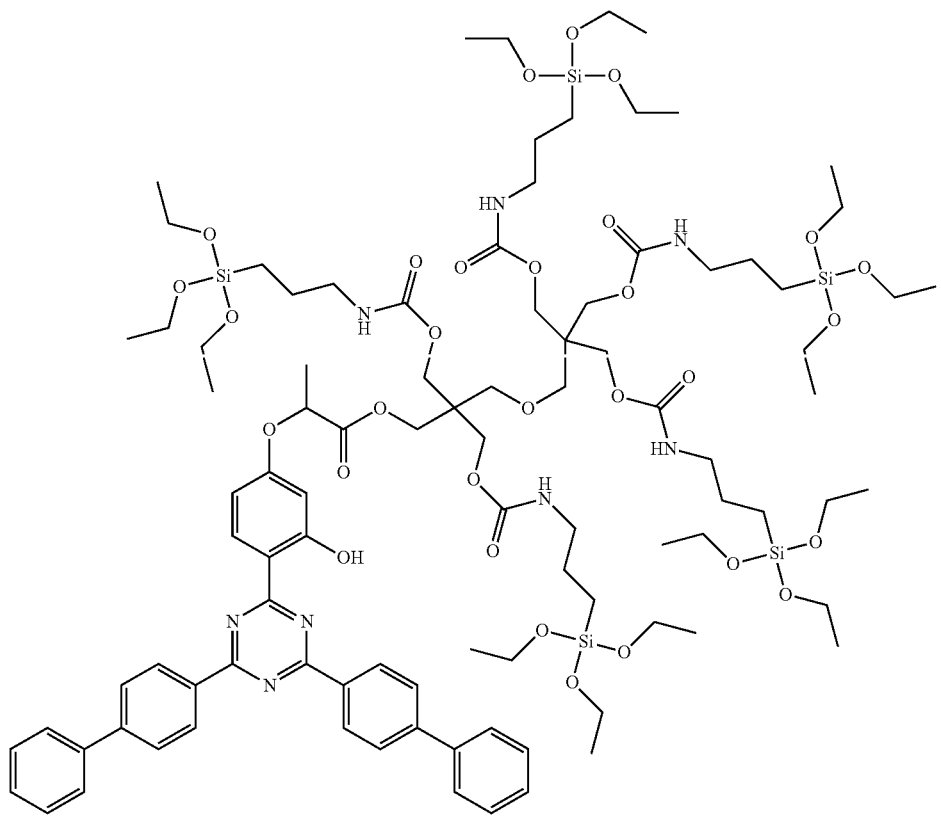
(I.8)
18. The coating composition according to claim 14, wherein P represents a mono-, di- or tri-alkoxysilane group and wherein alkoxy represents methoxy, ethoxy or (2-methoxy)-ethoxy.
19. The coating composition according to claim 14, wherein r is 1.
* * * * *

UNITED STATES PATENT AND TRADEMARK OFFICE
CERTIFICATE OF CORRECTION

PATENT NO.        : 8,715,406 B2
APPLICATION NO.   : 13/318182
DATED             : May 6, 2014
INVENTOR(S)       : Meyer Zu Berstenhorst et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 81 days.

Signed and Sealed this

Twenty-ninth Day of September, 2015

Michelle K. Lee
*Director of the United States Patent and Trademark Office*